US00RE46470E

(19) United States
(12) Reissued Patent
Tolvanen

(10) Patent Number: US RE46,470 E
(45) Date of Reissued Patent: Jul. 11, 2017

(54) SENSORY FOR MEASURING OF SIGNALS ON THE SURFACE OF THE SKIN AND METHOD FOR PRODUCING OF THE SENSORY

(71) Applicant: Suunto Oy, Vantaa (FI)

(72) Inventor: Pekka Tolvanen, Kuopio (FI)

(73) Assignee: Suunto Oy, Vantaa (FI)

(21) Appl. No.: 14/031,067

(22) Filed: Sep. 19, 2013

Related U.S. Patent Documents

Reissue of:
(64) Patent No.: 8,024,023
Issued: Sep. 20, 2011
Appl. No.: 11/399,786
Filed: Apr. 7, 2006

U.S. Applications:
(63) Continuation of application No. PCT/FI2004/000594, filed on Oct. 8, 2004.

(30) Foreign Application Priority Data

Oct. 8, 2003 (FI) ..... 20031476

(51) Int. Cl.
*A61B 5/04* (2006.01)
*A61B 5/00* (2006.01)
*A61B 5/024* (2006.01)
*A61B 5/0408* (2006.01)
*A61N 1/04* (2006.01)

(52) U.S. Cl.
CPC ..... *A61B 5/6805* (2013.01); *A61B 5/02438* (2013.01); *A61B 5/0408* (2013.01); *A61B 5/6804* (2013.01); *A61N 1/0484* (2013.01); *A61B 2562/125* (2013.01); *A61N 1/0452* (2013.01)

(58) Field of Classification Search
CPC A61N 1/0484; A61B 5/02438; A61B 5/0408; A61B 2562/125
USPC ..... 600/372, 395, 386, 388, 389, 396
See application file for complete search history.

(56) References Cited

U.S. PATENT DOCUMENTS

| | | | | |
|---|---|---|---|---|
| 5,184,620 | A | 2/1993 | Cudahy et al. | 128/639 |
| 5,374,283 | A * | 12/1994 | Flick | 607/46 |
| 5,624,736 | A * | 4/1997 | DeAngelis et al. | 428/196 |
| 6,151,528 | A | 11/2000 | Maida | 607/149 |
| 6,381,482 | B1 * | 4/2002 | Jayaraman et al. | 600/388 |
| 2003/0050550 | A1 * | 3/2003 | Schmidt et al. | 600/395 |

(Continued)

FOREIGN PATENT DOCUMENTS

| | | | |
|---|---|---|---|
| EP | 1090583 | A1 | 4/2001 |
| JP | 11128187 | A | 5/1999 |
| JP | 2002035141 | A | 2/2002 |

(Continued)

*Primary Examiner* — Jeffrey R. Jastrzab
(74) *Attorney, Agent, or Firm* — Seppo Laine Oy

(57) ABSTRACT

The present invention relates to sensory for measuring signals on the surface of the skin and for producing sensory. In the sensory in accordance with the invention, the electrode surfaces required for measuring of a signal and/or conductors required for transmitting of a signal have been fastened to the textile material of an outfit or accessory used on the body. In the method in accordance with the invention, the electrode surfaces required for the sensory and/or conductors are added to the textile material of an outfit or accessory used on the body.

20 Claims, 2 Drawing Sheets

NEW

(56) References Cited

U.S. PATENT DOCUMENTS

| | | | | |
|---|---|---|---|---|
| 2003/0163035 | A1 | 8/2003 | Van Heerden et al. | 600/397 |
| 2003/0186608 | A1* | 10/2003 | Goldberg | 442/304 |

FOREIGN PATENT DOCUMENTS

| | | | | |
|---|---|---|---|---|
| JP | 2002035141 | * | 5/2002 | A61B 1/04 |
| WO | WO 02/71935 | * | 2/2002 | A61B 5/024 |
| WO | WO 02071935 A1 | | 9/2002 | |

* cited by examiner

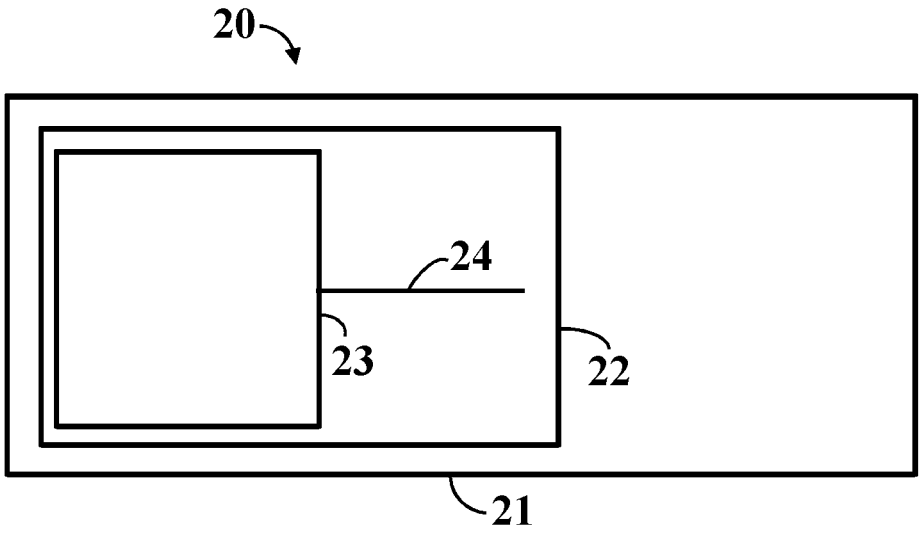
NEW FIGURE 8

SENSORY FOR MEASURING OF SIGNALS ON THE SURFACE OF THE SKIN AND METHOD FOR PRODUCING OF THE SENSORY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

The application is a continuation of International Patent Application No. PCT/FI2004/00594.

The present invention relates to sensory for recognizing and measuring signals on the surface of the skin. In addition, the present invention relates to a method for producing sensory.

BACKGROUND OF THE INVENTION

It is commonly recognized that by means of various kinds of sensors several signals in electrical form may be measured on the surface of the skin, such as:

electrical curve of heartbeat that is the ECG signal
electrical activity of muscles that is the EMG signal
electrical curve of brain function that is the EEG signal
conductivity of the surface of the skin
respiration rate
percentage of fat
intracellular and extracellular fluid balance in the body In sensories today in use, two or several electrodes are typically used, between which an electrical signal describing the potential difference is measured and which signal is transmitted for further processing in an electronic device. Measuring electrodes mentioned earlier are either separate electrodes to be attached on the skin one by one or electrode groups comprising several electrode surfaces, or various constructions placed on outfits, belts, bands or similar to be worn by a person, in which case several individual electrode surfaces in those are situated on the skin in defined places and in defined order.

Electrodes in clinical measurements are fastened with glue or a suction cup on the skin and the quality of a signal is secured by means of a special gel or similar improving conductivity. Outside clinical environment, for instance, during a physical exercise these kinds of electrodes have proved to be unpractical despite their reliability.

Sensories so-called heart rate monitors meant for monitoring a physical exercise are based on recognizing heartbeat by means of a sensor placed on the chest. The sensor is typically a solid elastic band by shape (a sensor band) or an elastic textile belt (a sensor belt) or an outfit, to which conductive electrode constructions have been integrated. Most conductive electrode surfaces in sensor bands are fastened to a frame part, by means of which the electrodes are then placed against the skin. Typically, the frame part is not able to stick to the skin by itself but it needs a separate fastening part, for instance, an elastic band or belt.

Electrodes in a sensor band are usually made of electro conductive plastics. The band is fastened on the chest by means of an elastic ribbon, the tightness of which is adjustable. As the plastic electrode surface is of solid material, there will by nature appear a wet space maintaining conductivity between the skin and the electrodes. Especially, during long performances and while sweating a lot, the band, however, slips away from its place or it may feel uncomfortable or cause abrasion. In addition, various disturbances are easily connected to measuring of a signal since the band as a solid construction is not elastic enough during motions normally included in the performance.

In a textile sensor band or similar outfit, the electrodes have been made of conductive textile or of conductive fibres, which are integrated to isolating textile in other way. While the textile construction in itself is permeable, on the outside of the textile electrode a separate layer holding moisture must be attached, for instance, by sewing, in which case sufficient conductivity is created between an electrode and the skin. The electrode constructions gathered in this way are attached to a belt or an outfit, for instance, by sewing. The belt or the outfit is put on in which case electrodes in them are placed on the chest to points where they stay in place as well as possible from the measuring point of view also during physical exercise. Especially, in outfit-type solutions, in places where the electrodes are, there will be thicker areas in the outfit fabric where the extra thickness due to the electrode textile and the layers holding moisture and their seams stiffen the fabric hindering the wearability of the outfit and causing disturbance for its part in the measurement. In addition, the most advantageous shape of textile electrode surfaces and moisturizing layers is usually square, as that shape is the most convenient to cut and to sew in manufacturing phase. A square shape is, however, not always the best shape in terms of measuring the actual signal, as, for instance, free and flexible shapes fitting as good as possible to the body anatomy are needed in measuring muscle activities.

Measuring heart rate during swimming or some other activity in water is especially complicated. Water may pass between the sensor band and the skin during swimming or in some other water activity, in which case impurities in the water (among other things salt, chlorine etc.) cause a short circuit between the electrodes of the band or some other means, in which case the measuring signal is disturbed. In addition, the flow resistance of water tends to move the band on the chest downwards the body, in which case the band is inconvenient to wear and causes friction slowening swimming.

Outfits on market with integrated electrodes in them have usually been made by adding conductive fibres or areas made of conductive material already in the manufacturing phase of the fabric or the outfit. Conductive fibres may be sewed among the own fibres of the ready fabric or they may be knitted or weaved straight to the structure of the fabric in the manufacturing phase. In other words, conductive material is either conductive fibre-like material or material is of fibre the surface of which has been made conductive. These fibres are then integrated to an outfit. Conductive material needs a supporting construction to be able to be attached to an outfit. These conductive fibres must also be made to a fibre-like form, as conductive fibre-like raw material does not exist. Electrode areas on outfits are also made by cutting off normal fabric from a ready outfit and fitting fabric made of conductive material or some other material to the area made in this way. Implementation of all outfits mentioned earlier requires special design and/or extra working phases, which increase manufacturing costs and which also partly changes the original usability characteristics of the outfit.

The object of the invention is to provide a sensory for measuring signals on the surface of the skin and a method for producing sensory, with the use of which disadvantages related to present methods are eliminated. Especially, the object of the invention is to provide sensory, which meets the shape and elasticity demands important from the signal-measuring point of view, and while using which the measuring electrodes stay in their place and in reliable contact also during a long-term measuring, heavy perspiration and various movements. In addition, sensory enables reliable and easy-to-use measurements also on users differing from each other by anatomy. Furthermore, the object of the invention is to provide a method, with the use of which sensory is able to be realized simply, advantageously and reliably.

BRIEF DESCRIPTION OF THE DRAWINGS

The foregoing aspects and other features of the invention are explained in the following description, taken in connection with the accompanying drawings, wherein:

*FIG. 8 shows sensory according to an embodiment of the present invention.*

DESCRIPTION OF THE INVENTION

Figure 1:
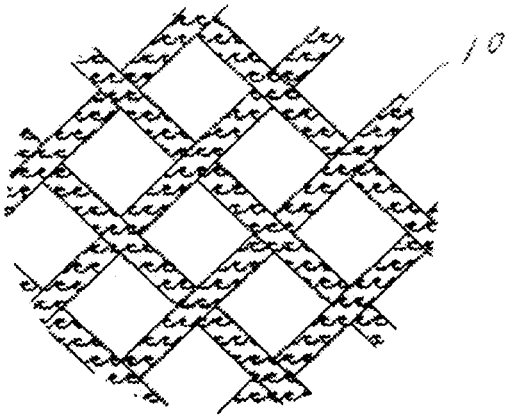
FIG. 1 is a view of an untreated fabric.

According to the invention, the electrode surfaces required for the measuring of a signal and/or conductors required for the transmission of a signal have been fastened to the textile material used on the body such as in an outfit or on accessories. Furthermore electrode construction includes conductive and impervious material placed together and multidimensionally, so that the construction is both conductive and essentially impervious to moisture. This kind of construction is advantageous because it keeps the region between the skin and the electrode electrically stable and conductive for signal measurement. However the electrode construction is such that it allows a portion of the moisture to permeate through the electrode. Still the amount of moisture between the skin and the electrode remains sufficient for stable measurement but it also prevents the electrode displacement e.g. due to excessive amount of sweat. In this context the word "essential" is used to describe the optimal balance of moisture within electrode surrounding.

Electrode's moisture penetration ability to maintain stable electroconductivity does not require fully tight technical structure. Therefore the electrode fine construction can be produced to meet the requirements of the application of use. For measurement where heavy sweating is expected (like in sport applications), the moisture penetration ability can be higher than in cases when sweating is not present (like in medical applications).

According to an embodiment of the invention, the electrode construction consists of conductive fibres and non-conductive fibres, which are knitted or weaved or sewn together in a manner that they form the desired conductive and essentially impervious construction. The conductive fiber may be made of any conductive material, which can be processed like a textile fibre. The non-conductive fiber is made of material which either is impervious to moisture or which is capable for holding moisture within its structure. Be selecting the processing parameters like fiber dimensions, number of fibres per surface area and/or per volume, the ability of the electrode to withhold moisture can be adjusted. When these conductive and non-conductive materials are processed together multidimensionally, the result construction is both conductive and essentially impervious to moisture.

According to an embodiment of the invention, the electrode surfaces required for the measuring of a signal and/or conductors required for the transmission of a signal have been fastened by coating to the textile material. In this way, the conductive surfaces are fastened straight to the material without any indirect supporting construction. For example, fabrics or other skin-tight outfits are these kinds of materials. In fabrics the conductive material is fastened straight to the own fibres of the fabric without any supporting construction. Electrode surfaces may even be manufactured to a ready outfit without any need to unravel or prepare the outfit itself. In case it is more advantageous, in manufactural sense, to produce the electrode surfaces in some manufacturing phase of the outfit the electrode surfaces may be attached straight to normal parts cut in accordance with patterns of the outfit. Therefore, there is no need to change the outfit, patterns of the outfit or the construction of the outfit for the attachment of electrodes. Electrode surfaces area part of the surface of the material, in which case they meet well the demands on shape and elasticity. In addition, they stay reliably and exactly in place. Furthermore, the thickness of an electrode surface formed in this way is remarkably thin, in which case the surface does not hinder the normal use of the material, for instance, of an outfit. In addition, the electrode surface sticks reliably to the material, because the seam in accordance with the invention takes place in the surface molecular level and covers the whole area. For instance, separate electrode surfaces attached by sewing may get loose if even one seam comes apart or starts to ravel out.

The band needed on the chest for measuring a heart rate may be secured such that the electrode surfaces are attached to a ready elastic ribbon, for example, bought from a draper's shop. In this case, both the measuring part and the elastic part of the band are of the same solid object, which is placed on the chest as flexible and reliable way as possible. For fastening the band one advantageous mechanical coupling or, for example, so-called Velcro-type strap fastening is enough. The necessary electronic part is fastened to the electrodes with as simple fastenings as possible, for example, with press-studs. In these ways savings are made in design, mould and manufacturing costs of mechanical parts in comparison with present sensor bands. In addition, from the user's point of view the change of the band part is advantageous in various situations, for example, when the ribbon is dirty or wet or worn out.

The integration of heart rate measurement, for example, to sports trousers may be provided by making the conductive electrode surfaces to the waistband, in which case the contact of the electrodes with the skin is made naturally tight enough. In addition, the electrodes may not move from their place thus minimizing the possibility of measuring disturbances.

Sensory in accordance with the invention comprises typically whatever usual wearable outfit or accessory or other object or material, may be placed against the skin, as well as one or several following things added to it:

electro conductive material attached or added to the surface of earlier mentioned outfits, accessories, objects or materials electric conductor, which has been fastened to the conductive material mentioned in the previous passage, and through which the signal is transmitted from the measuring point a connection, through which the conductor in accordance with the previous passage is connected to the electronics carrying out the signal processing.

An outfit in accordance with the invention may be, for example, a close-fitting shirt or trousers. A wearable, elastic or stiff object or accessory may be, for example, a belt fastened to the chest or to the pelvis, a sleeve, a leg or a band etc. fastened around a limb on muscles of the limb. An object to be placed on the skin may be, for example, a wristwatch, a sensor band or, for example, a mobile phone, which includes measuring and processing functions of an ECG signal. Material to be placed on the skin may be, for example, material to be fastened by means of friction, glue, a suction cup, adhesion or mechanical elements of micro size etc., which keeps it on the skin without a special attaching medium.

In sensory in accordance with the invention electrode surfaces have been shaped in accordance with the anatomy of the body and/or in a functional way in terms of measurements. In this case, they are always placed with respect to the body and on the skin such that they stay in their place as well as possible in terms of measurements also during physical exercise. Since conductive electrode surfaces and possible moisturizing layers are thin and elastic, they do not stiffen the fabric and, therefore, do not hinder usability of an outfit. In addition, the shape of electrode surfaces is the best possible in terms of signal measuring itself. For example, the electrode surfaces used for measuring muscle activity place exactly on muscles and muscle groups to be measured anatomically in a right way providing a signal as pure and undisturbed as possible as well as describing the load of the muscle in a right comparable way.

As many materials, especially textiles, are very elastic, the conductive surfaces to be fastened on them must be designed such that their shape stretches at least as much as the basic material itself such that there will appear no fractures or breaks on the conductor during use. A suitable shape is a wave-like line, which wave shape straightens when stretching but there will not be locally such a stretch that the conductivity would break up. Another alternative is a network-type structure, which stretches due to the loops of the network both as in plane and three-dimensionally.

In the method in accordance with the invention, the electro conductive electrode surfaces and/or conductors required for transmitting the signal required for sensory are added to the textile material of an outfit or accessory, which material is used on the body. Furthermore conductive and impervious materials are placed together and multidimensionally to form electrode construction, which is both conductive and essentially impervious to moisture. In the method sensory is provided to an outfit, accessory, object or material to be naturally placed on the skin. By means of the method, sensory may be carried out effectively, simply and advantageously especially in great manufacturing quantities.

In a method in accordance with the invention, conductive electrode surfaces are added by coating to the textile material. In an advantageous method in accordance with the invention, the electrode surface is created by vaporizing a conductive layer of a substance, which is suitable for the purpose, to a ready-made outfit or to the desired places in patterned and cut fabric for manufacturing such an outfit. In advantageous applications, among other things silver/silver chloride (Ag/AgCl) or silicon, of which a diamond surface is made, is used as conductive material or other suitable conductive material for fastening is used. The manufacturing of a conductive surface is carried out in a vaporizing chamber, where an outfit or piece of fabric is suitably placed together with a mask, where the perforation in accordance with the shapes of required electrode surfaces is made. The other characteristics of the conductive layer are defined by regulating circumstances and dose in the vaporizing chamber. The advantages of this kind of manufacturing method are, among other things, the free shapability of electrode surfaces and advantageousness of manufacturing especially in great manufacturing quantities. In addition, as there is no need for additional materials adding the thickness and stretching in different ways as well as fastening seams of those materials, usability characteristics of the outfit do not change. In case an outfit requires a layer for keeping moisture on the skin for improving conductivity, one can be made on the outer surface of the textile at the point of electrodes in some recognized way, such as a thin film fastened by printing technique.

Further, by using vaporizing method, electrode surfaces can be made, which are vaporized to a layer fastened to the textile and which improves moisture and conductivity. Depending on materials and their characteristics vaporizing can also be made first to the material, after which it is fastened to an outfit. Some polymers may be utilized as this kind of material.

Another way of manufacturing an electrode surface in accordance with the invention is fastening of an electro conductive plastic, silicone, rubber, or polymer material to textile by using laminating, printing, low-pressure injection moulding, or some other technique based on using liquid material or melting of material. Electrode surface may be manufactured by means of the method always into desired shape and elasticity. Special advantage of this method is the fact that at the same time in the electrode there will appear a surface conducting electricity and forming of sufficient moisture and maintaining conductivity. As an example there is an outfit, to which electrodes are moulded in an injection moulding machine, where the outfit may freely be placed such that only the spots required for electrodes, are inside the mould. By choosing the characteristics for conducting material to be used and by adjusting preset values of the injection moulding machine the electrode surfaces to be moulded are made to stick firmly and permanently to the outfit fabric such that material, however, does not necessarily penetrate the fabric. Cooling of the mould used for moulding is realized such that the textile placed in the mould for the time of moulding is not damaged although there may be a need to use positionally and temporarily greater temperatures than the durability of the textile for moulding an electrode.

An advantageous manufacturing method in accordance with the invention is so-called soft lithography, in which a stiff mask used in the traditional photolithography is replaced with a soft and flexible construction made of elastomer. This kind of construction makes it possible to exploit the lithography method also on the surface of a curved or three-dimensional object, for example, on a leg of an outfit placed on a cylindrical mould. For example, a mask, a stamp or a mould can be made of elastomer, by means of which a conductive surface is generated by photolithography to textile. The fine structure of the generated electrode may be, for example, a matrix network, which has the same flexibility etc. characteristics as the textile on which the network has been generated. The soft lithography may be applied on many various materials and surface chemistries. The applying of the method does not, for example, require a clean room, thus being also advantageous in that way.

In another manufacturing method of an electrode based on the applying of the soft lithography, a polymer film is fastened on the textile first by means of some recognized method, and then on this polymer a network, grooves etc. shapes equivalent to conductive areas is exposed by means of a mask, to which shapes a conductive layer is then generated. Also in this case, depending on materials and their characteristics, the generation may also be carried out first to the material, which is then fastened to an outfit. In the electrodes produced by this method, the polymer film acts as a layer improving the moisture and conductivity between the skin and the electrode.

The signal from electrodes produced by applying every method described earlier is conducted to other equipment by means of recognized conductors. A conductor is fastened to an electrode surface either afterwards by applying recognized connecting techniques or the conductors may be integrated to the textile before producing the electrode surface, in which case the connection between them is generated already in the production process of the electrode surface itself.

In an advantageous application, conductors are made by the same production method as the electrodes, in which case the areas required by the conductors have been designed to be a part of masks, moulds or some other construction applied in the producing and needed in the methods. In this kind of method, the areas of conductors in textile are coated afterwards with isolating material, such that there would be necessary isolation between conductors and the skin to keep the signal from electrodes as undisturbed as possible.

The construction of a conductive surface produced in accordance with the invention may be created such that it in itself prevents or limits the exit of moisture. For example, a surface made by moulding of electro conductive plastics is completely impervious to moisture. Penetration of moisture of conductive surface produced by vaporizing depends on the size of loops of the seams of the fabric and the thickness of the coating. Penetration of the conductive surface may be set suitable for the purpose, for example, by the choice of the loop size or by regulating the thickness or viscosity of the material forming the conductive surface, in which case in the electrode area either holes of desired size will be generated or it will be completely tight.

A layer essentially impervious to moisture may also be produced such that impervious to moisture material coats the fibres of the fabric itself thoroughly with a layer of desired thickness leaving the loops between the seams open. When a conductive coat is vaporized on this such that it covers previously mentioned layer impervious to moisture, a desired electrode surface is generated. In this case, the conductive layer is in fact placed on the layer impervious to moisture, or in other words, the substance impervious to moisture is placed inside the conductive layer. When a fabric treated in this way is placed on the skin, the moisture on the surface of it will surround every individual fibre, in which case the ions in the moisture may move between the skin and the conductive surface through the entire volume of the fabric. The surface area of the skin and the conductive surface will become remarkably larger than in case the surface was a planar area against the skin. Such the conductive and impervious to moisture material are not placed planar on top of each other but, together and multidimensionally placed, they form a construction, which is both conductive and essentially impervious to moisture.

Figure 2:
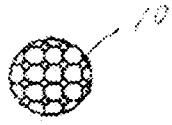
FIG. 2 is a cross sectional view of one of the fibers shown in FIG. 1.
Figure 3:
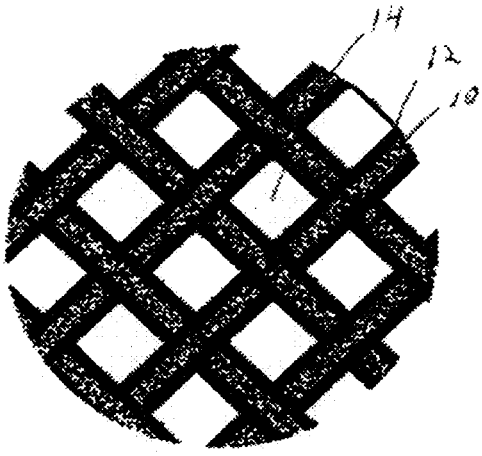
FIG. 3 is a view of the fabric of FIG. 1 with impervious to moisture material penetrating and coating the fabric.
Figure 4:
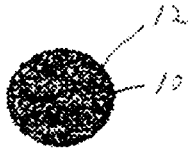
FIG. 4 is a cross sectional view of one of the fibers shown in FIG. 3.
Figure 5:
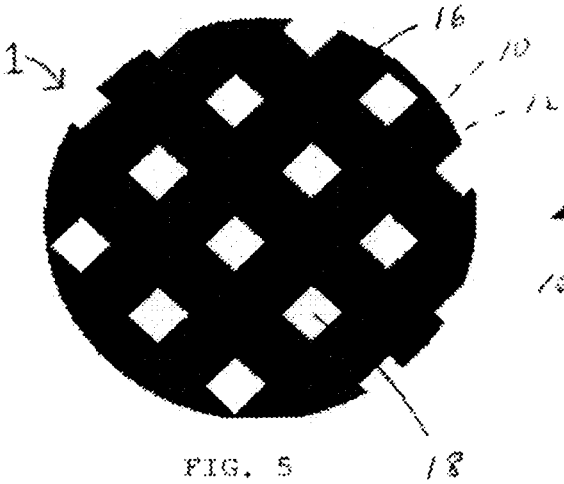
FIG. 5 is a view showing the fabric and material of FIG. 3 with a conductive coat.
Figure 6:
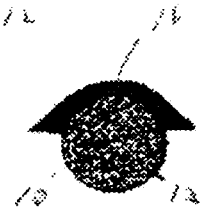
FIG. 6 is a cross sectional view of one of the fibers shown in FIG. 5.
Figure 7:
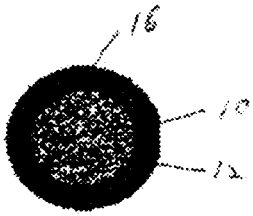
FIG. 7 is a cross sectional view of an alternate embodiment of one of the fibers shown in FIG. 5.

An example of this is shown in FIGS. 1-7. FIGS. 1 and 2 show a sample of untreated fabric 10. FIGS. 3-4 show the untreated fabric of FIGS. 1 and 2 having the impervious to moisture material 12 penetrating and coating the fabric 10 leaving loops 14 between the material open. FIG. 5 illustrates a portion of an outfit 1 according to one or more exemplary embodiments of the invention wherein there is shown the conductive coat 16 on the fabric and impervious to moisture material. FIG. 6 shows a partial covering of the conductive coat 16 and FIG. 7 shows a full covering of the conductive coat 16. Open areas 18 are still provided.

*Sensory according to an exemplary embodiment of the present invention is shown in FIG. 8. As shown, the sensory 20 comprises: a textile material 21, at least one non-conductive material layer 22 fastened by coating on the textile material 21, a conductive electrode surface 23 fastened by coating on the non-conductive material layer 22 and a conductor 24 fastened by coating on the non-conductive material layer 22.*

In an advantageous application of the invention, the electrodes required for measuring the heart rate are placed on a swimming suit or similar outfit worn in water. In swimming trunks, the place is on the waist area of trunks. In other swimming suits, electrodes may be placed also such that they are near the chest. It is recognized that the surroundings of electrodes and the outfit fabric on electrodes may be tightened and impregnated with material or a film, impervious to water, which, on one hand prevents the access of water between electrodes and the skin and, on the other hand isolates electrodes from each other. With the method in accordance with the invention, measuring outfits used in water may be produced by adding isolating material around electrodes such that desired tightness and isolating characteristics are achieved. For example, an area, somewhat larger than the desired electrode, may first be moulded of non-conductive silicone to an outfit, on which area the electrode surface itself of conductive silicone is moulded. The size, shape and the tightness of border areas of electrodes may be improved by moulding new suitably designed layers of isolating silicone on the earlier mentioned layers. In this case, a silicone layer impervious to moisture is generated around the electrodes and between an electrode and fabric, which layer prevents the access of moisture from outside to the conductive surface of the electrode placed against the skin. In addition, the transmitting of signals from electrodes to measuring electronics may be realized similarly tightened and isolated. While being a part of an outfit, this kind of construction adapts anatomically right against the body, in which case the additions to the swimwear caused by electrodes do not increase the kinetic friction between the body and water.

In an advantageous additional application some substance or layers added to the surface of the material worn on the body is made of absorptive material, to which gel, improving conductivity, lotion, moisturizing the skin, cream improving elasticity of the skin or some other chemical meant for conditioning the skin is absorbed. By means of absorbed substance the conductivity between the skin and the electrode surface and the permanency of conductivity may be improved, for example, when the measuring situation does not include perspiration more than normally or when the skin type of the person measured is naturally dry, tight or in other ways disadvantageous in terms of measuring.

The invention is not limited to the presented advantageous application but it can vary within the frames of the idea of the invention formed in the claims.

The invention claimed is:

[1. Sensory for measuring signals on the surface of the skin, comprising:

conductive electrode surfaces for measuring signals fastened by a coating on textile material of an outfit configured to be worn on a body directly on the skin, forming a conductive coating, and the conductive coating covering fibers of the textile itself thoroughly with a layer of desired thickness leaving loop areas between the coated fibers open and being formed to produce a membrane and effect an impervious nature of an electrode construction, wherein both the coating and an impervious material that form the construction are coated on the textile material, and the conductive coating and the impervious material are placed together overlapping each other in one plane to form the construction, which is both conductive and essentially impervious to moisture.]

[2. Sensory in accordance with claim 1, wherein the conductive electrode surfaces have been designed in accordance with anatomy of a body and/or in a functional way from a measuring point of view.]

[3. Sensory in accordance with claim 1, wherein the conductive electrode surfaces are flexible such that the shape of the surfaces stretches and damages weakening conductivity is not generated in the conductive surfaces.]

[4. Sensory in accordance with claim 1, wherein the fibers of the textile material comprise a first coating of the impervious material and then a subsequent coating of the conductive electrode surfaces leaving the open loop areas between the coated fibers.]

[5. Method for producing a sensory for measuring signals on the surface of the skin, comprising:

adding conductive electrode surfaces, for the sensory, by coating textile material of an outfit configured to be worn on a body directly on the skin, to form a conductive coating, the conductive coating covering fibers of the textile itself thoroughly with a layer of desired thickness leaving loop areas between the coated fibers open and being formed to produce a membrane and effect an impervious nature of an electrode construction, wherein both the coating and an impervious material that form the construction are coated on the textile material, and the conductive coating and the impervious material are placed together overlapping each other in one plane to form the construction, which is both conductive and essentially impervious to moisture.]

[6. Method in accordance with claim 5, in which a surface of the textile material is vaporized with an electro conductive material to form the conductive electrode surfaces.]

[7. Method in accordance with claim 5, in which a conductive electrode surface is produced of silver/silver chloride Ag/AgCl.]

[8. Method in accordance with claim 5, in which a conductive electrode surface is produced of silicon, in which case a diamond surface is created.]

[9. Method in accordance with claim 5, in which a conductive electrode surface is produced of a material, which is absorbed with a substance improving and/or maintaining moisture and conductivity of the skin.]

[10. Method in accordance with claim 5, in which electrodes of the electrode surfaces and material surrounding the electrodes are produced of conductive and non-conductive material such that access is prevented of external moisture and impurities between the electrodes and the skin and/or the electrodes are isolated from each other.]

[11. Method in accordance with claim 5, wherein the fibers of the textile material are first coated by the impervious material and then subsequently coated with the conductive electrode surfaces leaving the open loop areas between the coated fibers.]

*12. Sensory for measuring signals on the surface of the skin, comprising:*

*a textile material having loops,*

*at least one non-conductive material layer which is impervious to moisture fastened by coating on the textile material of an outfit or accessory,*

*conductive electrode surfaces for measuring signals fastened by coating on the non-conductive material layer configured to be worn on a body directly on the skin,*

*conductors for transmitting a signal from the conductive electrode surfaces, said conductors fastened by coating on the non-conductive material layer, and*

*wherein the at least one non-conductive material layer is fastened by coating on the textile material and the conductive electrode surfaces are fastened by coating on the non-conductive material layer such that the loops of the textile material are open.*

*13. Sensory in accordance with claim 12, wherein the conductors are coated with an isolating material.*

*14. Sensory in accordance with claim 12, wherein the conductive electrode surfaces and/or the conductors are electro conductive plastics, rubbers or polymers.*

*15. Sensory in accordance with claim 12, wherein the conductive electrode surfaces are flexible.*

*16. Sensory in accordance with claim 12, wherein the at least one non-conductive material layer has an area larger than the conductive electrode surfaces.*

*17. Sensory in accordance with claim 16, wherein the at least one non-conductive material layer surrounds the periphery of the conductive electrode surfaces.*

*18. Sensory in accordance with claim 12, wherein the conductors are each in electrical connection with a conductive electrode surface.*

*19. Sensory in accordance with claim 12, wherein the coating of at least one of the conductive electrode surfaces and conductors is a laminated coating.*

*20. Sensory in accordance with claim 12, wherein the coating of at least one of the non-conductive layer, conductive electrode surfaces and conductors is a vaporized coating.*

*21. A method for producing sensory for measuring signals on the surface of the skin comprising the steps of;*

*fastening at least one non-conductive material layer, which is impervious to moisture, by coating on a textile material of an outfit or accessory, said textile material having loops,*

*fastening conductive electrode surfaces by coating on the non-conductive material layer such that they are configured to be worn on a body directly on the skin,*

*fastening conductors, for transmitting a signal from the conductive electrode surfaces, by coating on the non-conductive material layer, and*

*wherein the at least one non-conductive material layer fastened by coating on the textile material and the conductive electrode surfaces are fastened by coating on the non-conductive material layer such that the loops of the textile material remain open.*

*22. A method according to claim 21, further comprising coating the conductors with an isolating material.*

*23. A method according to claim 21, wherein the conductive electrode surfaces and/or the conductors are electro conductive plastics, rubbers or polymers.*

*24. A method according to claim 21, wherein the at least one non-conductive material layer has an area larger than the conductive electrode surfaces which are fastened thereto, and the conductive electrode surfaces are fastened to the non-conductive material layer such that the non-conductive material layer surrounds the periphery of the conductive electrode surfaces.*

*25. A method according to claim 21, wherein the coating of at least one of the conductive electrode surfaces and conductors is lamination.*

*26. A method according to claim 21, wherein the coating of at least one of the non-conductive layer, conductive electrode surfaces and conductors is vaporization.*

*27. A method according to claim 21, wherein the conductive electrode surfaces and/or conductors are fastened to the non-conductive material layer prior to fastening the non-conductive material layer to the textile material.*

*28. A method according to claim 21, wherein the conductive electrode surfaces are produced by silver/silver chloride or silicon.*

*29. Sensory in accordance with claim 12, wherein the textile material is a woven textile material.*

*30. Sensory in accordance with claim 12, wherein the non-conductive material layer and conductive electrode surfaces are coatings of the textile material.*

*31. A method according to claim 21, wherein the textile material is a woven textile material and the non-conductive material layer and conductive electrode surfaces are coatings of the textile material.*

* * * * *